(12) United States Patent
Olson

(10) Patent No.: US 9,451,995 B1
(45) Date of Patent: Sep. 27, 2016

(54) ANTERIOR CERVICAL PLATE WITH FIXED ANGLE CAUDAL SCREWS

(71) Applicant: Training Research & Design, LLC, Danville, CA (US)

(72) Inventor: James H. Olson, Reno, NV (US)

(73) Assignee: Presidio Surgical, Inc., Danville, CA (US)

( * ) Notice: Subject to any disclaimer, the term of this patent is extended or adjusted under 35 U.S.C. 154(b) by 0 days.

(21) Appl. No.: 14/301,606

(22) Filed: Jun. 11, 2014

Related U.S. Application Data

(60) Provisional application No. 61/833,792, filed on Jun. 11, 2013.

(51) Int. Cl.
*A61B 17/80* (2006.01)
*A61B 17/70* (2006.01)

(52) U.S. Cl.
CPC ................. *A61B 17/7059* (2013.01)

(58) Field of Classification Search
CPC .............. A61B 17/7059; A61B 17/80; A61B 17/8061; A61B 17/8033; A61B 17/8042
USPC ..................... 606/70, 71, 280–299
See application file for complete search history.

(56) References Cited

U.S. PATENT DOCUMENTS

| 6,139,550 A * | 10/2000 | Michelson ......... A61B 17/1604 606/287 |
| 7,727,266 B2 * | 6/2010 | Lindemann ........ A61B 17/7059 606/289 |
| 2005/0075633 A1 * | 4/2005 | Ross .............................. 606/61 |

* cited by examiner

*Primary Examiner* — Ellen C Hammond
*Assistant Examiner* — Christina Negrellirodrigue
(74) *Attorney, Agent, or Firm* — Heisler & Associates

(57) ABSTRACT

The anterior cervical plate includes multiple pairs of holes passing therethrough including at least a pair of caudal holes and a pair of cephalad holes. The caudal holes pass through the anterior cervical plate at a fixed angle extending both in a caudal direction and toward a midline of the anterior cervical plate. The cephalad holes are configured to allow fastening screws to pass at differing angles through the cephalad holes. Windows are provided passing through the plate at locations between the pairs of caudal and cephalad holes. Locking plates are provided which pivotably attach to the plate in positions either covering or exposing the pairs of holes, to assist in keeping fastening screws securely attached to the anterior cervical plate.

13 Claims, 3 Drawing Sheets

ANTERIOR CERVICAL PLATE WITH FIXED ANGLE CAUDAL SCREWS

CROSS-REFERENCE TO RELATED APPLICATIONS

This application claims benefit under Title 35, United States Code §119(e) of U.S. Provisional Application No. 61/833,792 filed on Jun. 11, 2013.

FIELD OF THE INVENTION

The following invention relates to implantable medical devices configured to be affixed to the spine for support thereof. More particularly, this invention relates to anterior cervical plates which are configured to be attached by screws anteriorly to the cervical spine.

BACKGROUND OF THE INVENTION

When the cervical spine (neck) of an individual requires support, it is known in the prior art to attach a cervical plate to cervical vertebrae within the spine to hold the cervical vertebrae relative to each other. Such reinforcement of the cervical spine is indicated in situations such as where the vertebra of the spine have degenerated due to disease, or where a spinal injury has occurred, or otherwise where a medical professional determines that reinforcement of the cervical spine is warranted.

Known prior art cervical plates include anterior cervical plates which are placed on an anterior (i.e. front) side of the cervical spine. For instance, see U.S. Pat. No. 7,686,806 to Rhyne, incorporated herein by reference in its entirety. While such anterior cervical plates are known in the prior art, applicant has devised improvements to such anterior cervical plates. In particular, it is desirable that the cervical plate be easy to install reliably and precisely where desired, and for the anterior cervical plate to facilitate such precise positioning, both through its configuration and through its utilization with associated tools, such as bone drill guide jigs, drills, bending tools, tapping bits and fastening screws.

SUMMARY OF THE INVENTION

With this invention an anterior cervical plate is provided which is configured to be easy to install precisely where desired and to provide a high degree of support for the cervical spine and to be readily and easily positioned precisely where desired and with associated fastening screws positioned precisely where desired for maximum effectiveness.

In particular, the anterior cervical plate can have a variety of different lengths ranging from 12 millimeters to 96 millimeters. When shorter than 30 millimeters, typically the plate would have four holes for fastening to the cervical spine. When having between 30 and 55 millimeters of length, the cervical plate would typically have six holes as particularly depicted in the figures herein depicting one embodiment of this invention. When the cervical plate is longer than 55 millimeters, an eight hole variation would typically be provided.

In each embodiment, the anterior cervical plate has a pair of matching holes laterally spaced from each other in a manner having equal distance from upper and lower (i.e. cephalad and caudal) ends of the anterior cervical plate. The entire anterior cervical plate preferably is bilaterally symmetrical about a vertical center line and has a substantially constant thickness of approximately 2.0 millimeters. Due to the relatively thin nature of the anterior cervical plate, it can be quite lightweight, but benefits from being as strong as possible, such as by utilizing titanium or titanium alloys in the construction thereof. Other biocompatible materials could also be utilized in alternative embodiments of this invention.

Preferably, large windows are provided along the center line and between each set of laterally spaced holes in the anterior cervical plate. These windows allow the surgeon to have good visibility of the spine while placing the anterior cervical plate. Each hole receives a separate fastening screw therein utilizing screws such as those existing in the prior art for fastening of cervical plates to the cervical spine. The caudal holes are distinct from the other holes of the anterior cervical plate as described in detail below.

In particular, the caudal holes in an exemplary embodiment are configured so that each of the caudal screws angle in toward the center line of the anterior cervical plate and a center line of the cervical spine by 6°. Furthermore, the caudal holes extend downwardly in a caudal direction at 6° relative to horizontal. These angles for the caudal screws are provided by appropriate configuration of the head of the caudal screw and edges of the caudal holes. These angles are fixed at 6° in toward the center line and 6° from horizontal in a caudal direction for maximum effectiveness according to this invention. Most preferably, no variation from this amount is allowed. In alternative embodiments, this orientation of the caudal holes could be modified slightly (e.g. up to 10° or down to an angle below horizontal) to suit the needs of a particular surgeon, and still provide some of the benefits of this invention, with 6° considered to be optimal when reinforcing the cervical spine in many instances.

In contrast, the cephalad holes and any medial holes between the cephalad holes and caudal holes are not so particularly fixed in orientation. Rather, the cephalad holes and medial holes, as well as the cephalad screws and medical screws are configured so that they can vary in orientation preferably approximately 10° in any direction away from perpendicular to a surface of the anterior cervical plate. Thus, the surgeon has some degree of flexibility in positioning the cephalad screws and medial screws through the cephalad holes and medial holes.

Each pair of holes is preferably selectively covered by a singular locking plate which pivots to selectively leave the holes accessible or covered. The locking plates are preferably substantially planar and have a plate screw at a center point thereof. The plate screw is preferably captured to the anterior cervical plate so that the locking plates cannot fall off of the anterior cervical plate, even when loosened. As the plate screws are rotated, the locking plate goes from being tight to loose relative to the anterior cervical plate. When the locking plate is loose it can be readily rotated. When the locking plate is tight, the locking plate resists rotation.

In one embodiment, a pair of posts preferably extend from a rear of the locking plate. These posts preferably have a shape which matches a shape of a torque applying tool which is utilized to apply torque to the screws. Thus, when the locking plate is in position, these posts reside within the screws' torque applying heads and keep the attachment screws from rotating. In this way, the anterior cervical plate is kept tightly secured to the cervical spine. The locking plate can effectively keep the attachment screws securely attached even if the locking plate only covers a portion of the heads of the attachment screws.

Other features of the anterior cervical plate in various embodiments include providing screws which vary from 10 to 20 millimeters in length, configuring the anterior cervical plate to be pre-lordosed to have a lordosis angle of 8° between upper and lower edges of the anterior cervical plate. The anterior cervical plate is preferably formed of a material which can work with a bender tool which can bend the anterior cervical plate to increase or decrease this lordosis angle. The anterior cervical plate can work with screws which have been color coded so that screws such as caudal screws which are configured to only work with the caudal holes can be matched by color to ensure proper placement thereof.

Other tools which can work with the anterior cervical plate include an appropriately configured removal tool, temporary fixation pins, screw hex driver, variable drill guide, fixed drill guide, 10 to 20 millimeter pre-sized drill guides, an extractor and a cervical awl. These tools can be provided in a kit along with the anterior cervical plate for use during a surgical procedure.

In such a typical surgical procedure after the cervical spine has been exposed on an anterior side and the anterior cervical plate is ready for installation, the surgeon would initially identify an anterior cervical plate having a desired size (which step could occur preceding the surgical procedure). The anterior cervical plate can then be temporarily positioned where desired utilizing pins passing through the various holes in the anterior cervical plate. Once the anterior cervical plate is temporarily affixed where desired utilizing these pins, or alternatively some other form of clamp means, a drill guide is utilized for drilling holes into the bone.

This drill guide is preferably configured so that it nests within the various different holes in a manner which causes the holes to be precisely drilled where desired. In particular and with the caudal holes, the drill guide would be configured so that it nests properly with the caudal holes so that a drill passing through the drill guide drills a hole precisely 6° in a caudal direction from horizontal and 6° toward a center line relative to the anterior cervical plate. After the drill guide is in place, an appropriate drill is provided and a hole is drilled having a length similar to that of the fixation screws to be utilized.

After all of the holes have been drilled, a tapping tool can be utilized to tap threads into the holes formed in the vertebra. Alternatively, fasteners which are self-tapping can be utilized. After the tapping tool has been utilized, the drill guide can be removed. Appropriate fixation screws are then lined up with the holes in the anterior cervical plate with removal of any pins in the way, and a torque applying tool is utilized to fasten the fixation screws into the appropriate holes.

After each pair of screws have been so inserted, the locking plate can be loosened, rotated and re-tightened to secure the fixation screws in position. After all of the fixation screws are in place and all of the locking plates have been placed in their final horizontal position overlying the heads of the fixation screws and tightened, post anterior cervical plate implantation surgical procedures can be performed to complete the operation.

OBJECTS OF THE INVENTION

Accordingly, a primary object of the present invention is to provide an anterior cervical plate with caudal screw holes which support caudal screws at a fixed caudal angle angling both inwardly and downwardly for most effective cervical spine attachment.

Another object of the present invention is to provide a cervical plate with locking plates to hold fastening screws securely in position, holding the anterior cervical plate to the cervical spine.

Another object of the present invention is to provide an anterior cervical plate which is easy to securely fasten to the cervical spine from an anterior direction.

Another object of the present invention is to provide an anterior cervical plate which can be sized various different sizes to accommodate cervical spines of different sizes.

Another object of the present invention is to provide a method for attaching the anterior cervical plate to the cervical spine.

Another object of the present invention is to provide a method for stabilizing the cervical spine and to provide strength support for the cervical spine.

Other further objects of the present invention will become apparent from a careful reading of the included drawing figures, the claims and detailed description of the invention.

DESCRIPTION OF THE PREFERRED EMBODIMENT

Figure 1:
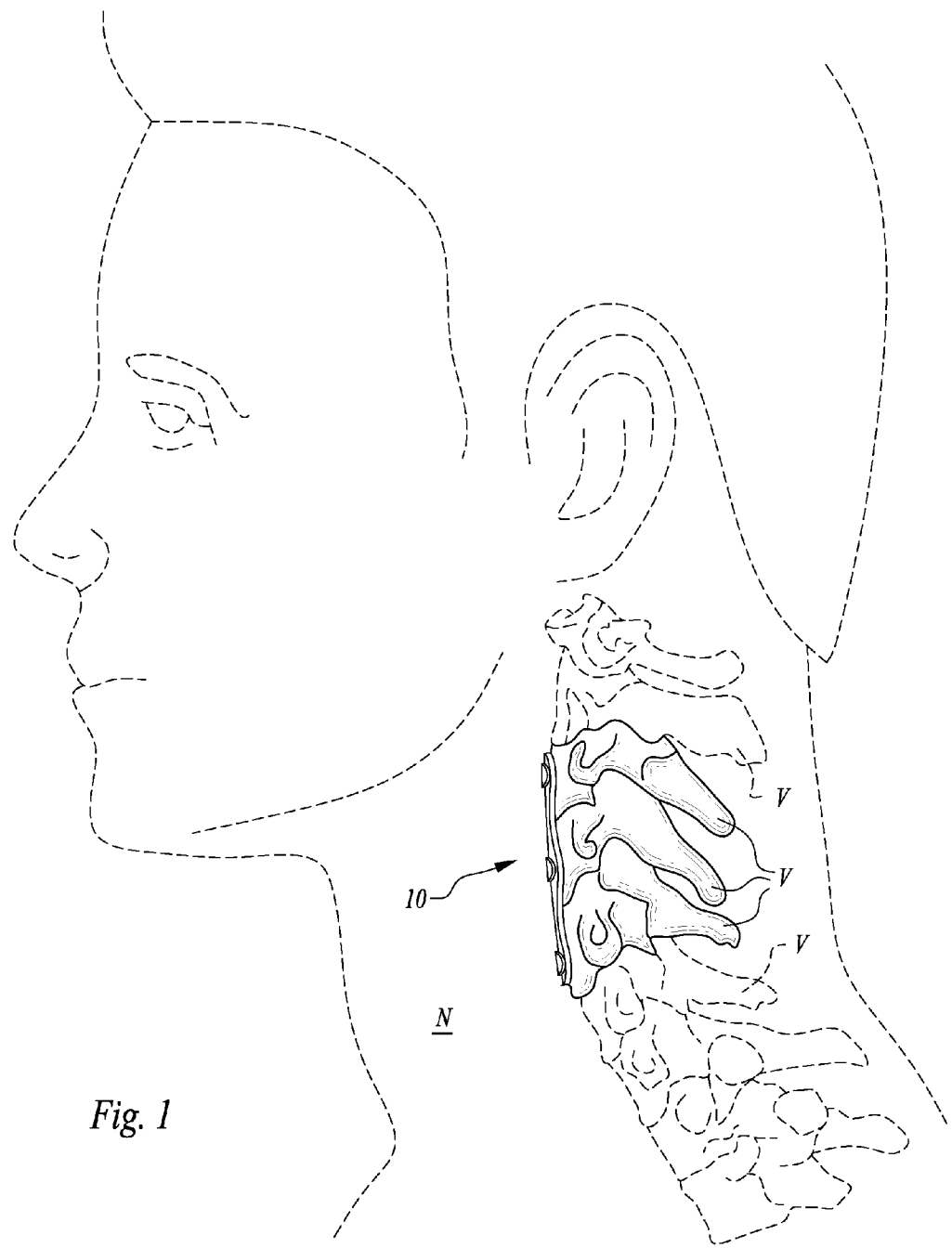
FIG. 1 is a side elevation view of the anterior cervical plate of this invention shown affixed to the cervical spine through multiple cervical vertebrae within the neck of a patient.
Figure 4:
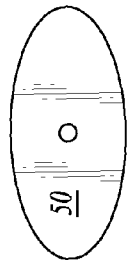
FIG. 4 is a front elevation view of the locking plate shown alone.

Referring to the drawings, wherein like reference numerals represent like parts throughout the various drawing figures, reference numeral 10 is directed to an anterior cervical plate for attachment anteriorly to the cervical spine vertebrae V in the neck N of a patient (FIG. 1). The plate 10 has various holes 40, 42, 44 (FIGS. 2 and 3) passing therethrough which receive fastening screws 30 in a particular fashion to optimize secure fastening of the anterior cervical plate 10 to the cervical vertebrae V (FIG. 1).

Figure 3:
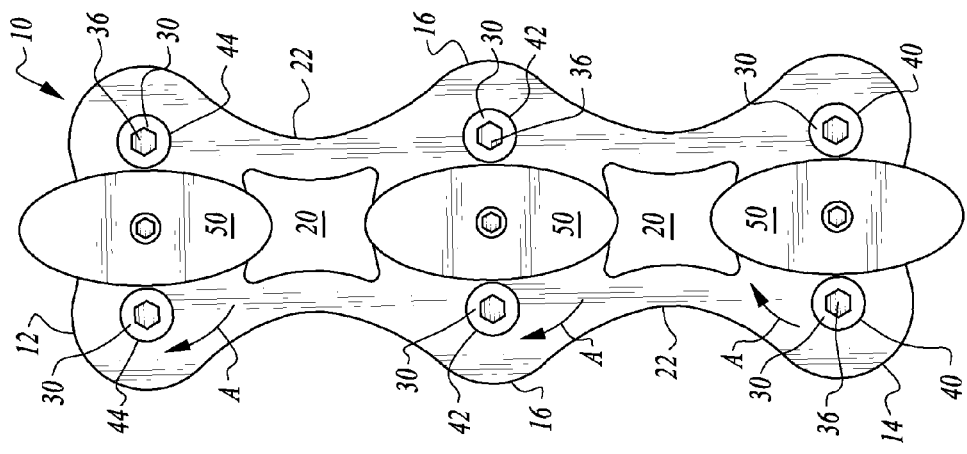
FIG. 3 is a front elevation view of that which is shown in FIG. 2 but with locking plates thereof shown in an open position with various fastener screw holes accessible and shown with screws therein.
Figure 2:
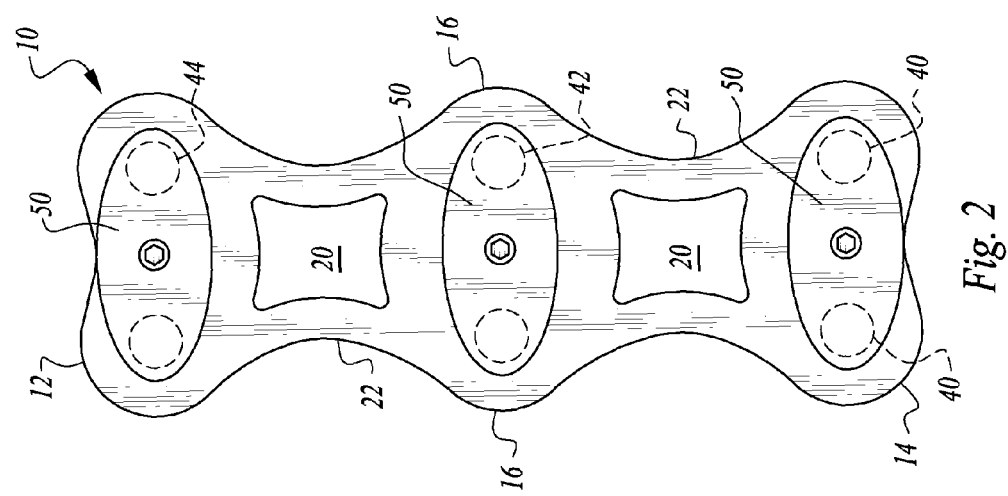
FIG. 2 is a front elevation view of the anterior cervical plate of this invention.
Figure 7:
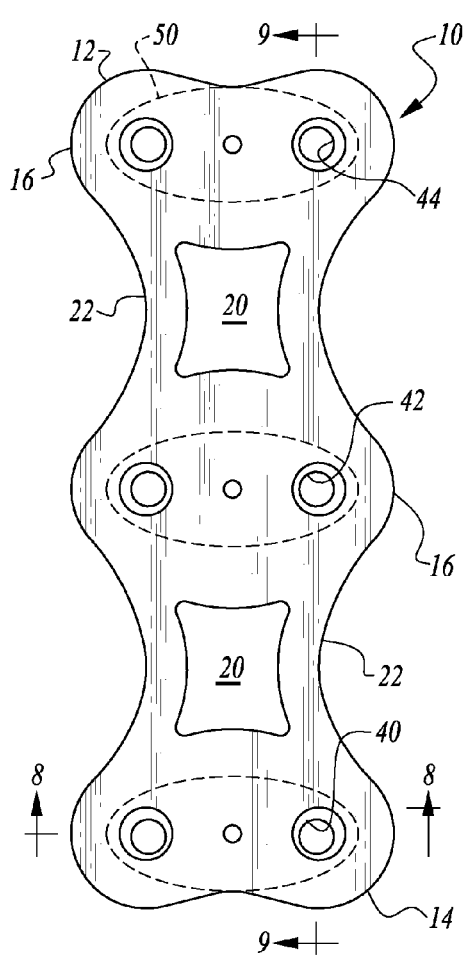
FIG. 7 is a front elevation view of the anterior cervical plate of this invention but with the locking plates removed.

In essence, and with particular reference to FIGS. 1-3, basic details of the anterior cervical plate 10 are described, according to a preferred embodiment. The plate 10 is a thin rigid structure of generally elongate form taller than it is wide. A series of windows 20 pass through the plate 10. Fastening screws 30 pass through various holes 40, 42, 44 in the plate 10. These screws 30 include bone threads to securely attach to vertebrae V adjacent the plate 10 (FIG. 1). A locking plate 50 is preferably provided over each pair of holes 40, 42, 44. The locking plate 50 is rotatable between two different positions, with one position covering the holes 40, 42, 44 and the other position exposing the holes 40, 42, 44.

More specifically, and with particular reference to FIGS. 2 and 3, basic details of the plate 10 geometry are described. The plate 10 has an elongate form extending between and upper end 12 opposite a lower end 14. A height of the plate 10 is generally defined as a distance between the upper end 12 and the lower end 14. The height typically varies between twelve and ninety-six millimeters. With shorter plates 10 only two pairs of holes 40, 44 are provided and with longer plates 10 four pairs of holes 40, 42, 44 are provided.

A pair of sides 16 extend between the upper end 12 and lower end 14. A width of the plate 10 is generally defined as the distance between these two sides 16. A thickness of the plate 10 is two millimeters in one embodiment. Preferably, the perimeter of the plate 10 is not linear, but rather follows a somewhat curving contour. On portions of the plate 10 where holes 40, 42, 44 are provided for attachment of fastening screws 30, the plate 10 is wider between the sides 16. In places where no such screws 30 are fastened, the width of the plate 10 between the sides 16 is narrower.

These narrower portions of the plate 10 preferably feature a window 20 passing through the plate 10. The embodiment of FIGS. 2 and 3 shows two such windows 20 and three pairs of holes 40, 42, 44. In other embodiments, as few as two pairs of holes 40, 44 might be provided, or more than three pairs of holes 40, 42, 44 could be provided. If only two pairs of holes 40, 44 are provided, only one window 20 would be provided. If four pairs of holes 40, 42, 44 are provided, three windows 20 would be provided.

Adjacent the windows 20 and at the sides 16, bights are formed in the sides 16, defining narrower portions of the plate 10 between the sides 16. The upper end 12 and lower end 14 are also preferably lobed somewhat so that they are slightly shorter between the upper end 12 and lower end 14 at a midline of the plate 10, than at a line aligned with the holes 40, 42, 44. In this way, a consistent amount of material is provided between a perimeter of the plate 10 and each of the holes 40, 42, 44. The windows 20 and bights 22 maximize visibility for the surgeon while preserving the strength around the holes 40, 42, 44.

While the plate 10 could be entirely planar, most preferably it exhibits a curving contour both when viewed from the side and when viewed from above or below. As viewed from the side (FIG. 9) curvature of the plate 10 is exhibited which causes a vertebral side of the plate 10 to be concave and an anterior side of the plate 10 to be convex. Angles of curvature relative to a midpoint include 4° of curvature above the midpoint and 4° of curvature below the midpoint, for a total of 8° of curvature.

Figure 9:
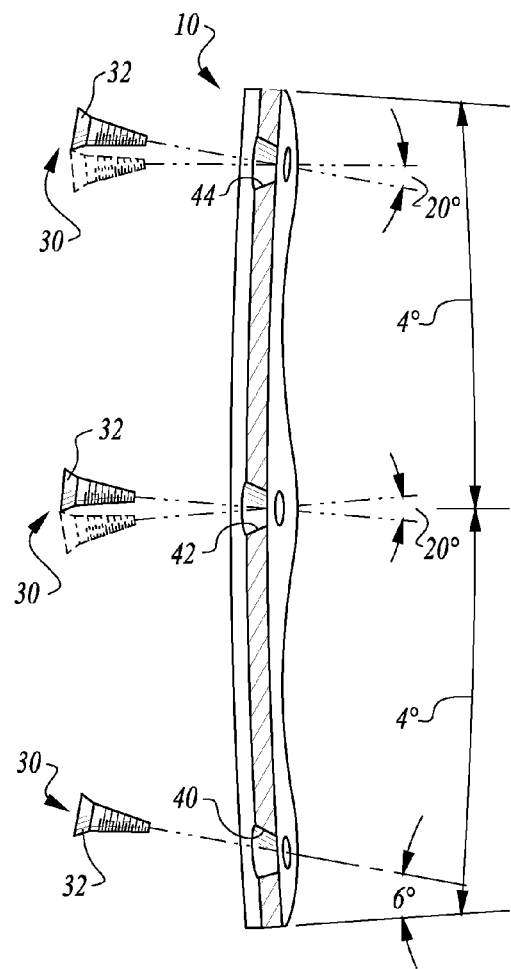
FIG. 9 is a side elevation view of that which is shown in FIG. 7 and with a series of fastening screws aligned with various holes therein.

When viewed from above or below (FIG. 8) the plate 10 also exhibits curvature. In one embodiment this curvature amount is the same as the lateral curvature (FIG. 9) so that the plate 10 forms a small section of a complete sphere. In other embodiments, the curvature when viewed from above or below is greater or less than the lateral curvature (FIG. 9). It is also conceivable that the plate 10 could be entirely flat or exhibit more curvature than that depicted herein.

Figure 8:
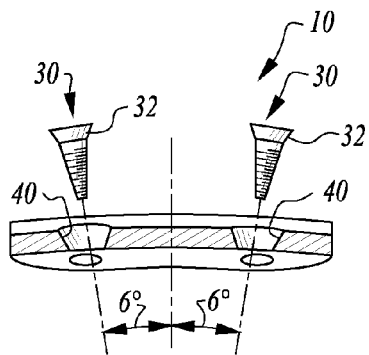
FIG. 8 is a bottom plan view of the anterior cervical plate of FIG. 7 and with fastening screws shown aligned with caudal holes thereof.
Figure 10:
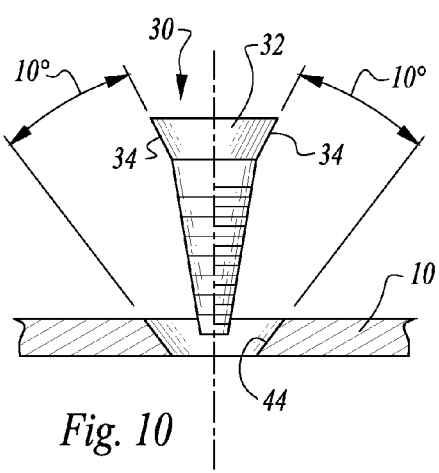
FIG. 10 is a detail of a portion of that which is shown in FIG. 9 showing details of a fastening screw and cephalad or medial hole in the anterior cervical plate.

With particular reference to FIGS. 8-10, particular details of the fastening screws 30 and holes 40, 42, 44 in the plate 10 are described, according to a preferred embodiment. The plate 10 includes a pair of caudal holes 40 defining two lowermost holes passing through the plate 10. These caudal holes 40 are closer to the lower end 14 than to the upper end 12. Preferably, the two caudal holes 40 are a similar distance from the lower end 14 (also called the "caudal end"). The caudal holes 40 are preferably angled to have a taper which matches a taper of a tapered edge 34 of a head 32 of fastening screws 30 provided to pass through the caudal holes 40 and secure the plate 10 to adjacent vertebrae V (FIG. 1).

The caudal holes 40 do not have a centerline perpendicular to the plate 10. Rather, a centerline of the caudal holes 40 is configured and the tapered sides of the caudal holes 40 are configured so that the fastening screws 30 passing through the caudal holes 40 will be encouraged toward a fixed angle which is 6° away from horizontal in a caudal (downward and toward the lower end 14) direction (FIG. 9). Furthermore, the caudal holes 40 are angled so that centerlines thereof angle toward a centerline between the caudal holes 40 of the plate 10, such as when viewed from above (FIG. 8). This angle is also preferably about 6°. In alternative embodiments, an angle of 10° or less could be provided, with 6° considered to be optimal. Thus, the caudal holes 40 encourage the fastening screws 30 to be securely attached thereto with an orientation which is angled downward 6° away from horizontal and inward toward a midline of the plate 10 by 6°. Such an orientation is considered to both avoid the fasteners being entirely parallel so that they more securely engage the adjacent vertebrae V, and also by being angled downward and also more securely engage the vertebrae V.

The plate 10 also includes cephalad holes 44. When the plate 10 has at least three pairs of holes 40, 42, 44, the plate 10 also includes medial holes 42. The cephalad holes 44 and medial holes 42 preferably also have tapered sides, but with the tapered sides exhibiting a greater angle than that of tapered edges 34 of the heads 32 of the fastening screws 30. In particular, extra taper of 10° (FIGS. 9 and 10) on either side between the head 32 of the fastening screws 30 and the tapered edge 34 of the cephalad holes 44 and medial holes 42 allow for some variation in orientation (20° total) of the fastening screws 30 as they pass through either the medial holes 42 or the cephalad holes 44. A medical professional can thus select an optimal orientation for the fastening screws 30 passing through the medial holes 42 and the cephalad holes 44, based on the particular bone morphology of the patient and to most securely attach the anterior cervical plate 10 to the vertebrae V in the cervical spine of the patient.

With particular reference to FIGS. 2-6, details of the locking plate 50 are described according to a most preferred embodiment. The locking plate 50 is provided to cover and secure the fastening screws 30 and to prevent the fastening screws 30 from becoming detached from the plate 10 after implantation of the plate 10. The locking plate 50 is a ridged structure preferably of oval form with a width dimension greater than a height dimension. This width dimension is selected to be slightly more than a distance between the pairs of holes 40, 42, 44, and with a height dimension which is slightly less than a distance between the pairs of holes 40, 42, 44. Thus, with the locking plate 50 affixed at a midpoint to the plate 10 with this midpoint between each pair of holes 40, 42, 44, the locking plate 50 can pivot about this attachment between two orientations. In a covering orientation (or position) the locking plate 50 extends horizontally and covers each of the adjacent holes 40, 42, 44. In an exposed orientation, the locking plate 50 has been rotated 90° (about arrow A of FIG. 3) and the adjacent fastening screws 30 are exposed.

Figure 5:
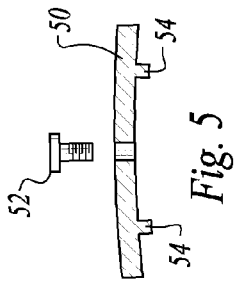
FIG. 5 is a bottom plan full sectional view of the locking plate of FIG. 4 and with a plate screw shown adjacent thereto and exploded away from a hole in the locking plate for supporting the locking plate screw.
Figure 6:
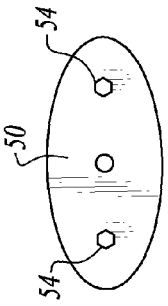
FIG. 6 is a rear elevation view of the locking plate of FIG. 4.

The locking plate 50 preferably has a slight curvature such as that generally matching a curvature of the plate 10 (FIG. 5). Most preferably, posts 54 extend from an undersurface of the locking plate 50 and a plate screw 52 passes through a hole at a midpoint of the locking plate 50. This plate screw 52 can thread into a threaded hole in the plate 10 between each pair of holes 40, 42, 44 to secure the locking plate 50 to the anterior cervical plate 10 in a manner allowing rotation of the locking plate 50 relative to the anterior cervical plate 10. As an alternative, some fastener other than the plate screw 52 could be provided, such as a rivet.

The posts 54 are spaced apart by a distance similar to a distance between the pair of holes 40, 42, 44 adjacent to the locking plate 50. These posts 54 can extend down into a torque recess 36 in the head 32 of each fastening screw 30 to assist in keeping the fastening screws 30 in position. In one embodiment, the posts 54 have an outer contour which matches a contour (or "fastener pattern") of the torque recess 36. For instance, the torque recess 36 can be hexagonal to receive an allen wrench. Posts 54 can similarly be hexagonal and of similar dimension. The fastening screws 30 can be rotated a precise amount with the tightening tool always stopping at a predictable orientation matching that for the posts 54 of the locking plate 50. The locking plate 50 can finally be rotated (about arrow A of FIG. 3) into the covering orientation and the posts 54 can drop down into the torque recess 36 and keep the torque recesses from being able to turn, thus allowing the locking plate 50 to lock the fastening screws 30 from inadvertent rotation.

Shapes other than hexagonal shapes could be provided for the posts 54 and still provide this locking feature. If desired, the posts 54 could be configured to be slightly smaller or otherwise angled so that the stopping point in rotation of the fastening screws 30 would not need to be precisely selected for the posts 54 to fit within the torque recesses 36 of the fastening screws 30, and still provide the basic function of keeping the fastening screws 30 from rotating an undesirable amount when the locking plate 50 has been oriented to the covering position.

In one embodiment, the locking plate 50 is sufficiently tight to the plate 10 and the posts 54 sufficiently long that the locking plate 50 needs to flex somewhat until the posts 54 snap noticeably into place within the torque recess 36 of the fasteners 30. In this way the medical professional has confidence when the locking plate 50 has been properly oriented to hold the fasteners 30.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. An anterior cervical plate, comprising in combination:
   a thin plate extending from an upper end to a lower end;
   a pair of caudal screw holes passing through said plate, each said caudal screw hole located closer to said lower end than to said upper end, each said caudal screw hole located a similar distance from said lower end;
   a pair of cephalad screw holes passing through said plate, said pair of cephalad screw holes located closer to said upper end than to said lower end, said pair of cephalad screw holes located a similar distance from said upper end;
   said caudal screw holes angled to support fastening screws extending through said caudal screw holes in a caudal direction away from perpendicular to said plate;
   wherein at least one locking plate is removably positionable overlying said pair of caudal screw holes when in a first caudal screw hole covering position;
   wherein said locking plate has a width greater than a distance between said caudal screw holes; and
   wherein said locking plate has a height which is less than a distance between said caudal screw holes, such that when said locking plate is rotated with said height oriented horizontally, said caudal screw holes are uncovered by said locking plate, and when said locking plate is rotated to orient said width extending horizontally, said locking plate overlies said caudal screw holes.

2. The plate of claim 1 wherein said caudal screw holes are angled away from horizontal by an amount greater than zero and less than 10° away from horizontal in a caudal direction.

3. The plate of claim 2 wherein said caudal screw holes are angled about 6° way from horizontal in a caudal direction.

4. The plate of claim 1 wherein said locking plate includes a pair of posts extending from a surface thereof adjacent said caudal screw holes at a distance similar to a distance between said caudal screw holes.

5. The plate of claim 4 wherein a pair of fastening screws are sized to pass through said caudal screw holes, said fastening screws including torque recesses therein, said posts able to extend into said torque recesses.

6. The plate of claim 5 wherein said torque recesses have a fastening pattern, said posts having a contour matching said fastening pattern of said torque recesses of said fastening screws.

7. The plate of claim 1 wherein said plate is angled between said upper end and said lower end with a curvature away from purely planar and vertical.

8. The plate of claim 1 wherein said plate is angled left to right, such that said plate is not entirely planar and adapted to wrap around the cervical spine somewhat when attached to said cervical spine anteriorly.

9. The plate of claim 1 wherein said pair of cephalad screw holes have side edges angled an amount greater than a taper of edges of heads of fastening screws passing through said cephalad screw holes.

10. An anterior cervical plate including:
    a substantially rigid mass having at least four holes and at least one window passing entirely from an anterior side to a posterior side thereof;

said holes configured to include a pair of caudal holes adjacent a caudal end of the plate and a pair of cephalad holes above the pair of caudal holes;

said caudal holes angled to receive caudal screws therethrough with the caudal screws extending along a line which extends substantially 6° from horizontal in a caudal direction;

wherein said caudal holes are angled about 6° toward a center line midway between the two caudal holes along a center line of the said plate;

wherein said locking plate has a height which is less than a distance between said caudal screw holes, such that when said locking plate is rotated with said height oriented horizontally, said caudal screw holes are uncovered by said locking plate, and when said locking plate is rotated to orient said width extending vertically, said locking plate overlies said caudal screw holes;

wherein said locking plate includes a pair of posts extending from a surface thereof adjacent said caudal screw holes at a distance similar to a distance between said caudal screw holes; and wherein a pair of fastening screws are sized to pass through said caudal screw holes, said fastening screws including torque recesses therein, said posts able to extend into said torque recesses, said torque recesses having a fastening pattern, said posts having a contour matching said fastening pattern of said torque recesses of said fastening screws.

11. The anterior cervical plate of claim 10 wherein other holes in said plate are adapted to provide variability of angular orientation for screws passing therethrough.

12. The anterior cervical plate of claim 10 wherein at least one locking plate is removably positionable overlying said pair of caudal screw holes when in a first caudal screw hole covering position.

13. The anterior cervical plate of claim 12 wherein said locking plate has a width greater than a distance between said caudal screw holes.

* * * * *